United States Patent [19]

Davis

[11] 4,136,043
[45] Jan. 23, 1979

[54] HOMOGENEOUS COMPOSITIONS PREPARED FROM DIMERCAPTOTHIADIAZOLES

[75] Inventor: Kirk E. Davis, Euclid, Ohio

[73] Assignee: The Lubrizol Corporation, Wickliffe, Ohio

[21] Appl. No.: 470,483

[22] Filed: May 16, 1974

Related U.S. Application Data

[63] Continuation-in-part of Ser. No. 380,914, Jul. 19, 1973, abandoned, and Ser. No. 459,428, Apr. 9, 1974, abandoned.

[51] Int. Cl.$^2$ .............................................. C10M 1/38
[52] U.S. Cl. ..................................... 252/47.5; 252/47; 252/391
[58] Field of Search .................. 252/16, 27, 47, 47.5, 252/314, 391; 200/128

[56] References Cited

U.S. PATENT DOCUMENTS

| | | | |
|---|---|---|---|
| 2,157,380 | 5/1939 | Abrams | 252/16 X |
| 2,764,547 | 9/1956 | Fields | 252/47 X |
| 2,844,541 | 7/1958 | Work | 252/314 |
| 2,910,439 | 10/1959 | Fields | 252/47 X |
| 3,032,430 | 5/1962 | Heller | 252/314 X |
| 3,219,666 | 11/1965 | Norman et al. | 252/51.5 A X |
| 3,533,943 | 10/1970 | Papay | 252/47 X |
| 3,775,321 | 11/1973 | Turnquest et al. | 252/47 X |
| 3,840,549 | 10/1974 | Blaha et al. | 252/47 X |

Primary Examiner—Delbert E. Gantz
Assistant Examiner—Andrew Metz
Attorney, Agent, or Firm—James W. Adams, Jr.; William H. Pittman

[57] ABSTRACT

Compositions which form homogeneous blends with lubricating oils and the like are produced by preparing a mixture of an oil-soluble dispersant (preferably a substantially neutral or acidic carboxylic dispersant) and a dimercaptothiadiazole, preferably 2,5-dimercapto-1,3,4-thiadiazole, usually with a diluent, especially a lubricant base liquid, and heating said mixture above about 100° C. The compositions often contain dimercaptothiadiazole moieties in amounts substantially greater than stoichiometric. They are useful for suppression of copper activity and "lead paint" deposition in lubricants.

17 Claims, No Drawings

HOMOGENEOUS COMPOSITIONS PREPARED FROM DIMERCAPTOTHIADIAZOLES

This application is a continuation-in part of copending applications Ser. No. 380,914, filed July 19, 1973, and Ser. No. 459,428, filed Apr. 9, 1974 both now abandoned.

This invention relates to new compositions of matter useful as lubricant additives, especially for the inhibition of copper activity and "lead paint" deposition in lubricants, and to lubricants containing such additives. More particularly, it relates to compositions obtained by preparing a mixture comprising at least one oil-soluble dispersant and at least one dimercaptothiadiazole and heating said mixture at a temperature above about 100° C. until it is capable of forming a homogeneous blend with an oleaginous liquid of lubricating viscosity.

Two phenomena sometimes encountered in internal combustion engine lubrication are copper activity and "lead paint" deposition. The first of these is a tendency of the lubricant to stain copper parts, and it frequently results from the use as additives of compounds containing "active sulfur" — that is, sulfur which is highly labile and reactive. The second phenomenon is the deposition on engine surfaces of a thin film of finely divided lead-containing material from the lead additives in the fuel; this problem is not alleviated by ordinary dispersants or detergents present in the lubricant. Both of these phenomena are undesirable and it is of interest to develop additives for their suppression.

It has been known for some time that derivatives of dimercaptothiadiazoles, especially of 2,5-dimercapto-1,3,4-thiadiazole, are effective additives for the inhibition of copper activity and many patents have issued on additives containing dimercaptothiadiazole nuclei. In the development of all of these additives, it has been necessary to find materials which react with the dimercaptothiadiazole to form oil-soluble products, since the dimercaptothiadiazoles themselves are not soluble in oil. An example of such an oil-soluble product, disclosed in U.S. Pat. No. 3,519,564, is prepared from one mole of hydrazine, two moles of carbon disulfide and about 1-2 equivalents (based on the number of basic nitrogen atoms therein) of an acylated polyamine dispersant. Under the alkaline conditions thus prevailing, the hydrazine, carbon disulfide and dispersant react to form a salt of 2,5-dimercapto-1,3,4-thiadiazole.

A principal object of the present invention is to provide new compositions of matter useful as lubricant additives.

A further object is to provide lubricant additives which are effective at suppressing sulfur activity and "lead paint" deposition.

A still further object is to provide new oil-soluble compositions containing the dimercaptothiadiazole nucleus.

A still further object is to prepare new and useful lubricants for internal combustion engines and the like.

Other objects will in part be obvious and will in part appear hereinafter.

The present invention is based on the discovery that at temperatures above about 100° C., usually about 100°–250° and especially about 120–200°, oil-soluble dispersants interact with amounts of dimercaptothiadiazoles considerably in excess of those expected on the basis of salt formation of the type disclosed in the aforementioned U.S. Pat. No. 3,519,564. The compositions thus obtained are capable of forming substantially stable homogeneous blends with lubricating liquids, which compositions contain higher proportions of dimercaptothiadiazole than those previously prepared and are effective for the purposes hereinbefore described.

The first essential starting material for the preparation of the compositions of this invention is a dimercaptothiadiazole. There are four such compounds possible, which are named and have structural formulas as follows:

2,5-Dimercapto-1,3,4-thiadiazole
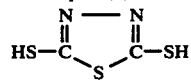

3,5-Dimercapto-1,2,4-thiadiazole
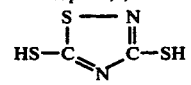

3,4-Dimercapto-1,2,5-thiadiazole
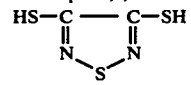

4,5-Dimercapto-1,2,3-thiadiazole
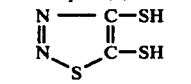

Of these the most readily available, and the one preferred for the purposes of this invention, is 2,5-dimercapto-1,3,4-thiadiazole. This compound will sometimes be referred to hereinafter as DMTD. However, it is to be understood that any of the other dimercaptothiadiazoles may be substituted for all or a portion of the DMTD.

DMTD is conveniently prepared by the reaction of one mole of hydrazine, or a hydrazine salt, with two moles of carbon disulfide in an alkaline medium, followed by acidification. For the preparation of the compositions of this invention, it is possible to utilize already prepared DMTD or to prepare the DMTD in situ, subsequently adding the dispersant or adding the DMTD to the dispersant as described hereinafter.

The second essential starting material is an oil-soluble dispersant. The materials chiefly contemplated are often known as "ashless dispersants", although, depending on its constitution, the dispersant may upon combustion yield a non-volatile material such as boric oxide or phosphorus pentoxide; however, it does not ordinarily contain metal and therefore does not yield a metal-containing ash on combustion.

Oil-soluble dispersants of many types are known in the art and are described in various patents. Any of them are suitable for use in preparing the compositions of this invention. The following are illustrative:

(1) Reaction products of carboxylic acids (or derivatives thereof) containing at least about 34 and preferably at least about 54 carbon atoms with nitrogen-containing compounds such as amines, organic hydroxy compounds such as phenols and alcohols, and/or basic inorganic materials. Examples of these products, referred to herein as "carboxylic dispersants", are described in British Pat. No. 1,306,529 and in many U.S. patents including the following: U.S. Pat. No. 3,163,603 U.S. Pat. No. 3,184,474 U.S. Pat. No. 3,215,707 U.S. Pat. No. 3,219,666 U.S. Pat. No. 3,271,310 U.S. Pat. No.

| | |
|---|---|
| 3,272,746 U.S. Pat. No. | 3,281,357 U.S. Pat. No. |
| 3,306,908 U.S. Pat. No. | 3,311,558 U.S. Pat. No. |
| 3,316,177 U.S. Pat. No. | 3,340,281 U.S. Pat. No. |
| 3,341,542 U.S. Pat. No. | 3,346,493 U.S. Pat. No. |
| 3,351,552 U.S. Pat. No. | 3,381,022 U.S. Pat. No. |
| 3,399,141 U.S. Pat. No. | 3,415,750 U.S. Pat. No. |
| 3,433,744 U.S. Pat. No. | 3,444,170 U.S. Pat. No. |
| 3,448,048 U.S. Pat. No. | 3,448,049 U.S. Pat. No. |
| 3,451,933 U.S. Pat. No. | 3,454,607 U.S. Pat. No. |
| 3,467,668 U.S. Pat. No. | 3,501,405 U.S. Pat. No. |
| 3,522,179 U.S. Pat. No. | 3,541,012 U.S. Pat. No. |
| 3,542,678 U.S. Pat. No. | 3,542,680 U.S. Pat. No. |
| 3,567,637 U.S. Pat. No. | 3,574,101 U.S. Pat. No. |
| 3,576,743 U.S. Pat. No. | 3,630,904 U.S. Pat. No. |
| 3,632,510 U.S. Pat. No. | 3,632,511 U.S. Pat. No. |
| 3,697,428 U.S. Pat. No. 3,725,441 U.S. Pat. No. Re 26,433. 3,567,637 U.S. Pat. No. 3,271,310 U.S. Pat. No. | |
| 3,433,744 U.S. Pat. No. | 3,574,101 U.S. Pat. No. |
| 3,272,746 U.S. Pat. No. | 3,444,170 U.S. Pat. No. |
| 3,576,743 U.S. Pat. No. | 3,281,357 U.S. Pat. No. |
| 3,448,048 U.S. Pat. No. 3,630,904 | |

(2) Reaction products of aliphatic or alicyclic halides containing at least about 30 carbon atoms with amines, preferably polyalkylene polyamines. These may be characterized as "amine dispersants" and examples thereof are described, for example, in the following U.S. Pat. Nos. 3,275,554 3,438,757 3,454,555 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:
U.S. Pat. Nos. 3,413,347 3,697,574 3,725,277 3,725,480 3,726,882.

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.

| | | | | |
|---|---|---|---|---|
| 3,036,003 | 3,087,936 | 3,200,107 | 3,216,936 | 3,254,025 |
| 3,256,185 | 3,278,550 | 3,280,234 | 3,281,428 | 3,282,955 |
| 3,312,619 | 3,366,569 | 3,367,943 | 3,373,111 | 3,403,102 |
| 3,442,808 | 3,455,831 | 3,455,832 | 3,493,520 | 3,502,677 |
| 3,513,093 | 3,533,945 | 3,539,633 | 3,573,010 | 3,579,450 |
| 3,591,598 | 3,600,372 | 3,639,242 | 3,649,229 | 3,649,659 |
| 3,658,836 | 3,697,574 | 3,702,757 | 3,703,536 | 3,704,308 |
| 3,708,522 | | | | |

(5) Interpolymers of oil-solubilizing monomers containing a pendant alkyl group having at lest about 8 carbon atoms, such as decyl methacrylate, vinyl decyl ether or a relatively high molecular weight olefin, with monomers containing polar substituents, e.g., aminoalkyl acrylates, aminoalkyl acrylamides or poly-(oxyalkylene)-substituted alkyl acrylates. These may be characterized as "polymeric dispersants" and examples thereof are disclosed in the following U.S. Pat. Nos. 3,329,658 3,449,250 3,519,565 3,666,730 3,687,849 3,702,300

The pertinent disclosures of all of the above-noted patents are incorporated by reference herein.

The carboxylic dispersants are the preferred ones for use in the preparation of the compositions of this invention. They may be most conveniently and accurately described in terms of radicals A and B present therein. Radical A is at least one acyl, acyloxy or acylimidoyl radical containing at least about 34 carbon atoms. The structures of these radicals, as defined by the International Union of Pure and Applied Chemistry, are as follows (R representing a hydrocarbon or similar group):

Radical B is preferably at least one radical in which a nitrogen or oxygen atom is attached directly to said radical A, said nitrogen or oxygen atom also being attached to a hydrocarbon radical or substituted hydrocarbon radical, especially an amino, alkylamino-, polyalkyleneamino-, hydroxy- or alkyleneoxy-substituted hydrocarbon radical. With respect to radical B, the dispersants are conveniently classified as "nitrogen-bridged dispersants" and "oxygen-bridged dispersants" wherein the atom attached directly to radical A is nitrogen or oxygen, respectively.

The nitrogen-bridged dispersants, which will be described first, are those disclosed (for example) in the above-mentioned U.S. Pat. Nos. 3,219,666 and 3,272,746 which also describe a large number of methods for their preparation. The nitrogen-containing group therein is derived from compounds characterized by a radical of the structure > NH wherein the two remaining valences of nitrogen are satisfied by hydrogen, amino or organic radicals bonded to said nitrogen atom through direct carbon-to-nitrogen linkages. These compounds include aliphatic, aromatic, heterocyclic and carbocyclic amines as well as substituted ureas, thioureas, hydrazines, guanidines, amidines, amides, thioamides, cyanamides and the like.

Especially preferred as nitrogen-containing compounds used in the preparation of the nitrogen-bridged dispersants are alkylene polyamines and hydroxyalkyl-substituted alkylene polyamines. The alkylene polyamines comprise, in general, alkylene amines containing about 10 or less alkylene groups joined through nitrogen atoms. They include principally the ethylene amines, propylene amines, butylene amines and homologs thereof, and also piperazines and aminoalkyl-substituted piperazines. Hydroxyalkyl-substituted derivatives of these alkylene polyamines are also contemplated for use in preparing the nitrogen-bridged dispersant. Typical examples of suitable amines are ethylene diamine, triethylene tetramine, pentaethylene hexamine, propylene diamine, tri-propylene tetramine, di-(trimethylene) triamine, 1,4-bis-(2-aminoethyl)piperazine, 1-(2-aminopropyl)piperazine, N-(2-hydroxyethyl)ethylene diamine, 1-(2-hydroxyethyl)piperazine, and 2-heptadecyl-1-(2-hydroxyethyl)-imidazoline. Mixtures of these amines may also be used.

The preferred amines are the polyethylene polyamines containing from two to about eight amino groups per molecule. A commercially available mixture of polyethylene polyamines containing an average of about 3-7 amino groups per molecule is particularly suitable.

The acylating agent used for preparing the nitrogen-bridged dispersant is a carboxylic acid-producing compound containing at least about 34 and preferably at least about 54 carbon atoms. By "carboxylic acid-proreacted with the hydrocarbon source as previously described.

Oxygen-bridged dispersants comprise the esters of the above-described carboxylic acids, as described (for example) in the aforementioned U.S. Pat. Nos. 3,381,022 and 3,542,678. As such, they contain acyl or, occasionally, acylimidoyl radicals as radical A. (An oxygen-bridged dispersant containing an acyloxy radical as radical A would be a peroxide, which is unlikely to be stable under all conditions of use of the compositions of this invention.) These esters are preferably prepared by conventional methods, usually the reaction (frequently in the presence of an acidic catalyst) of the carboxylic acid-producing compound with an aliphatic compound such as a monohydric or polyhydric alcohol or with an aromatic compound such as a phenol or naphthol. The preferred hydroxy compounds are alcohols containing up to about 40 aliphatic carbon atoms. These may be monohydric alcohols such as methanol, ethanol, isooctanol, dodecanol, cyclohexanol, neopentyl alcohol, monomethyl ester of ethylene glycol and the like, or polyhydric alcohols including ethylene glycol, diethylene glycol, dipropylene glycol, tetramethylene glycol, pentaerythritol, glycerol and the like. Carbohydrates (e.g., sugars, starches, cellulose) are also suitabe as are partially esterfied derivatives of polyhydric alcohols having at least three hydroxy radicals.

The reaction is usually effected at a temperature above about 100° C. and typically at 150°-300° C. The esters may be neutral or acidic, or may contain unesterified hydroxy groups, according as the ratio or equivalents of acid-producing compound to hydroxy compound is equal to, greater than or less than 1:1.

As will be apparent, the oxygen-bridged dispersants are normally substantially neutral or acidic. They are among the preferred dispersants for the purposes of this invention.

It is possible to prepare mixed oxygen- and nitrogen-bridged dispersants by reacting the acylating agent simultaneously or, preferably, sequentially with nitrogen-containing and hydroxy reagents such as those previously described. The relative amounts of the nitrogen-containing and hydroxy reagents may be between about 10:1 and 1:10, on an equivalent weight basis. The methods of preparation of the mixed oxygen- and nitrogen-bridged dispersants are generally the same as for the individual dispersants described, except that two sources of radical B are used. As previously noted, substantially neutral or acidic dispersants are preferred, and a typical method of producing mixed oxygen- and nitrogen-bridged dispersants of this type (which are especially preferred) is to react the acylating agent with the hydroxy reagent first and subsequently react the intermediate thus obtained with a suitable nitrogen-containing reagent in an amount to afford a substantially neutral or acidic product.

Typical carboxylic dispersants suitable for use in preparing the compositions of this invention are listed in Table I. "Reagent A" and "Reagent B" are, respectively, the sources of radicals A and B as previously defined. The dispersants of Examples 1-6, 8, 9, 12 and 14-17 are basic; those of the other examples are substantially neutral or acidic.

TABLE 1

| Example | Reagent A | Reagent B | Ratio of equivalents, A:B | Reaction temperature, °C. | Diluent | Acid or base no. |
|---|---|---|---|---|---|---|
| 1 | Polyisobutenyl (mol. wt. about 900) succinic anhydride prepared from chlorinated polyisobutene | Polyethylene amine mixture containing about 3-7 amino groups per molecule | 0.48 | 150 | Mineral oil | 50B |
| 2 | Same as Example 1 | Pentaethylene hexamine | 0.41 | 150 | Mineral oil | 82B |
| 3 | Like Example 1 except polyisobutene mol. wt. is about 1050 | Pentaethylene hexamine | 0.61 | 150 | Mineral oil | 130B |
| 4 | Like Example 1, except polyisobutene mol. wt. is about 850 | Diethylene triamine | 1.0 | 150 | Mineral oil | 19B |
| 5 | Same as Example 4 | Ethylene diamine | 1.0 | 150 | Mineral oil | 19B |
| 6 | Same as Example 4 | Di-(1,2-propylene)triamine | 1.0 | 180-190 | Mineral oil-toluene | — |
| 7 | Same as Example 4 | N-(2-hydroxyethyl)-trimethylene diamine | 1.06 | 150-155 | Mineral oil | 4 |
| 8 | Tetrapropenyl succinic anhydride | Triethylene tetramine | 1.0 | 155 | Toluene | 60B |
| 9 | Same as Example 1 | Same as Example 1 | 0.67 | 150 | Mineral oil | |
| 10 | Same as Example 1 | Same as Example 1 | 1.33 | 150 | Mineral oil | 6B |
| 11 | Like Example 1, except polyisobutene mol. wt. is about 1100 | Pentaerythritol, followed by polyethylene amine of Example 1 (ratio of equivalents 7.7:1) | 0.44 | 150-210 | Mineral oil | 2B |
| 12 | Isostearic acid | Pentaethylene hexamine | 0.8 | 150 | Mineral oil | 8B |
| 13 | Acid produced by reaction of chlorinated (3.6%Cl) polyisobutene (mol. wt. 750) with KCN, followed by hydrolysis | Ethylene diamine | 2.0 | 150 | Xylene | — |
| 14 | Methyl ester produced by reaction of chlorinated (4.7%Cl) (mol. wt. 1000) with methyl methacrylate | Triethylene tetramine polyisobutene | 1.0 | 140-220 | — | — |
| 15 | Reaction product of sodio-malonic ester with $C_{75}$ brominated wax | Same as Example 1 | 0.4 | 150 | Xylene | — |
| 16 | Reaction product of chlorinated (4.5%Cl) polyisobutene (mol. wt. 850) with acrylic acid | Pentaethylene hexamine | 0.8 | 180-200 | — | — |
| 17 | Acid produced by haloform reaction with methyl heptacontanyl ketone | Same as Example 1 | 0.8 | 180-210 | — | — |
| 18 | Same as Example 11 | Pentaerythritol | 0.5 | 150-210 | Mineral oil | — | ducing compound" is meant an acid, anhydride, acid halide, ester, amide, imide, amidine or the like; the acids and anhydrides are preferred.

The acylating agent is usually prepared by the reaction (more fully described hereinafter) of a relatively low molecular weight carboxylic acid-producing compound with a hydrocarbon source containing at least about 30 and preferably at least about 50 carbon atoms. The hydrocarbon source should be substantially saturated, i.e., at least about 95% of the total number of carbon-to-carbon covalent linkages should be saturated. It should also be substantially free from pendant groups containing more than about six aliphatic carbon atoms. It may be a substituted hydrocarbon source; by "substituted" is meant sources containing substituents which do not alter significantly their character or reactivity. Examples are halide, hydroxy, ether, keto, carboxy, ester (especially lower carbalkoxy), amide, nitro, cyano, sulfoxy and sulfone radicals. In general, not more than three and usually not more than one such radical will be present for each 10 carbon atoms.

The preferred hydrocarbon sources are those derived from substantially saturated petroleum fractions and olefin polymers, particularly polymers of monoolefins having from 2 to about 30 carbon atoms. Thus, the hydrocarbon source may be derived from a polymer of ethylene, propene, 1-butene, isobutene, 1-octene, 3-cyclohexyl-1-butene, 2-butene, 3-pentene or the like. Also useful are interpolymers of olefins such as those illustrated above with other polymerizable olefinic substances such as styrene, chloroprene, isoprene, p-methylstyrene, piperylene and the like. In general, these interpolymers should contain at least about 80%, preferably at least about 95%, on a weight basis of units derived from the aliphatic monoolefins.

Another suitable hydrocarbon source comprises saturated aliphatic hydrocarbons such as highly refined high molecular weight white oils or synthetic alkanes.

In many instances, the hydrocarbon source should contan an activating polar radical to facilitate its reaction with the low molecular weight acid-producing compound. The preferred activating radicals are halogen atoms, especially chlorine, but other suitable radicals include sulfide, disulfide, nitro, mercaptan, ketone and aldehyde groups.

As already pointed out, the hydrocarbon sources generally contain at least about 30 and preferably at least about 50 carbon atoms. Among the olefin polymers those having a molecular weight of about 700-5000 are preferred, although higher polymers having molecular weights from about 10,000 to about 100,000 or higher may sometimes be used. Especially suitable as hydrocarbon sources are isobutene polymers within the prescribed molecular weight range, and chlorinated derivatives thereof.

Any one of a number of known reactions may be employed for the incorporation of the hydrocarbon source into the acid-producing compound to provide the required acylating agent. Thus, an alcohol of the desired molecular weight may be oxidized with potassium permanganate, nitric acid or a similar oxidizing agent; a halogenated olefin polymer may be reacted with a ketene; an ester of an active hydrogen-containing acid, such as acetoacetic acid, may be converted to its sodium derivative and the sodium derivative reacted with a halogenated high molecular weight hydrocarbon such as brominated wax or brominated polyisobutene; a high molecular weight olefin may be ozonized; a methyl ketone of the desired molecular weight may be oxidized by means of the haloform reaction; an organometallic derivative of a halogenated hydrocarbon may be reacted with carbon dioxide; a halogenated hydrocarbon or olefin polymer may be converted to a nitrile, which is subsequently hydrolyzed; or an olefin polymer or its halogenated derivative may undergo an addition reaction with an unsaturated acid or derivative thereof. This latter reaction is preferred, especially where the acid-producing compound is maleic acid or anhydride. The resulting product is then a hydrocarbon-substituted succinic acid or derivative thereof. The reaction leading to its formation involves merely heating the two reactants at about 100°-200° C. The substituted succinic acid or anhydride thus obtained, may, if desired, be converted to the corresponding acid halide by reaction with known halogenating agents such as phosphorus trichloride, phosphorus pentachloride or thionyl chloride.

For the formation of the nitrogen-bridged dispersant, the hydrocarbon-substituted succinic anhydride or acid, or other acylating agent, and the alkylene polyamine or other nitrogen-containing reagent are heated to a temperature above about 80° C., preferably about 100°-250° C. The product thus obtained has predominantly amide, imide and/or amidine linkages (containing acyl or acylimidoyl groups). The process may in some instances be carried out at a temperature below 80° C. to produce a product having predominantly salt linkages (containing acyloxy groups). The use of a diluent such as mineral oil, benzene, toluene, naphtha or the like is often desirable to facilitate control of the reaction temperature.

The relative proportions of the acylating agent and the alkylene polyamine or the like are such that at least about one-half the stoichiometrically equivalent amount of polyamine is used for each equivalent of acylating agent. In this regard it will be noted that the equivalent weight of the alkylene polyamine is based upon the number of amine radicals therein, and the equivalent weight of the acylating agent is based on the number of acidic or potentially acidic radicals. (Thus, the equivalent weight of a hydrocarbon-substituted succinic acid or anhydride is one-half its molecular weight.) Although a minimum of one-half equivalent of polyamine per equivalent of acylating agent should be used, there does not appear to be an upper limit for the amount of polyamine. If an excess is used, it merely remains in the product unreacted without any apparent adverse effects. Ordinarily, no more than about 2 equivalents of polyamine are used per equivalent of acylating agent.

Especially preferred for the purposes of this invention are substantially neutral or acidic dispersants; that is, dispersants having a base number less than 7 or an acid number when titrated to a bromphenol blue end point. ("Acid number" is the number of milligrams of potassium hydroxide required for titration of a 1-gram sample, and "base number" is the number of milligrams of potassium hydroxide equivalent to the amount of acid required for titration of a 1-gram sample.) Nitrogen-bridged dispersants of this type may often be prepared by using one equivalent or less of polyamine per equivalent of acylating agent.

In an alternative method for producing the nitrogen-bridged dispersant, the alkylene polyamine is first reacted with a low molecular weight, unsaturated carboxylic acid-producing compound such as maleic anhydride and the resulting intermediate is subsequently TABLE 1-continued

| Example | Reagent A | Reagent B | Ratio of equivalents, A:B | Reaction temperature, °C. | Diluent | Acid or base no. |
|---|---|---|---|---|---|---|
| 19 | Like Example 1, except polyisobutene mol. wt. is about 1000 | Neopentyl glycol | 1.0 | 240–250 | — | — |
| 20 | Same as Example 19 | Methanol* | Excess methanol | 50–65 | Toluene | — |
| 21 | Same as Example 19 | Polyethylene glycol (mol. wt. about 600) | 2.0 | 240–250 | — | — |
| 22 | Same as Example 19 | Oleyl alcohol** | 1.0 | 150–173 | Xylene | 0 |
| 23 | Like Example 16, except polyisobutene mol. wt. is about 982 | Sorbitol | 0.48 | 115–205 | Mineral oil | — |
| 24 | Same as Example 23 | Pentaerythritol | 1.0 | 180–205 | — | — |
| 25 | Reaction product of polyisobutene (mol. wt. 1500) with chloroacetyl chloride | Mannitol | 0.33 | 115–205 | Mineral oil | — |

*Hydrogen chloride catalyst
p-Toluenesulfonic acid catalyst

The compositions of this invention are formed by preparing a mixture of DMTD with the dispersant and heating said mixture within the temperature range previously recited, for a period of time sufficient to provide a product which is capable of forming a homogeneous blend with an oleaginous liquid of lubricating viscosity, usually with a lubricating oil such as the natural and synthetic lubricants described hereinafter. The mixture will usually also contain an organic liquid diluent which may be either polar on non-polar. Suitable polar liquids include alcohols, ketones, esters and the like. As non-polar liquids there may be used petroleum fractions, ordinarily high-boiling distillates such as mineral oils of lubricating viscosity, as well as naphthas and intermediate fractions (e.g., gas oil, fuel oil or the like). Also suitable are aromatic hydrocarbons, especially the higher boiling ones such as xylene and various minimally volatile alkylaromatic compounds. Halogenated hydrocarbons such as chlorobenzene may also be used.

It is preferred to use the above-described oleaginous liquids of lubricating viscosity as diluents, since this permits the direct use of the composition as a lubricant or a concentrate for incorporation in lubricants. Especially suitable are mineral oils of the paraffinic, naphthenic, or mixed paraffinic-naphthenic types and oils derived from coal or shale. Also suitable but less preferred are animal and vegetable oils (e.g., castor oil, lard oil) and synthetic lubricating oils. The latter include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); alkylbenzenes (e.g., dodecylbenzenes, tetradecylbenzenes, dinonylbenzenes, di-(2-ethylhexyl)benzenes, etc.); polyphenyls (e.g., biphenyls, terphenyls, etc.); and the like. Alkylene oxide polymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for examples, the acetic acid esters, mixed $C_3$-$C_8$ fatty acid esters, or the $C_{13}$ Oxo acid diester of tetraethylene glycol. Another suitable class of synthetic lubricating oils comprises the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethyl-hexanoic acid, and the like. Silicon-based oils such as the polyalkyl-, polyaryl-, polyalkoxy- or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-tetraethyl) silicate, tetra-(p-tert-butyl-phenyl) silicate, hexyl-(4-methyl-2-pentoxy)-disiloxane, poly(methyl)-siloxanes, poly(methylphenyl)-siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans, and the like.

In a particularly preferred embodiment, the nonpolar organic liquid diluent is mineral oil of lubricating viscosity. It is also contemplated, though not preferred, to use a volatile liquid initially and subsequently replace it by mineral oil, with the volatile liquid being removed by distillation, vacuum stripping or the like or to dissolve the DMTD in a volatile polar liquid such as an alcohol and to add the resulting solution to the dispersant-oil mixture, removing the volatile liquid by flash stripping or other evaporation methods.

The relative amounts of dispersant and DMTD may vary widely, as long as a homogeneous product is ultimately obtained. Thus, about 0.1–10 parts by weight of dispersant may be used per part of DMTD. More often, about 5–10 parts of dispersant are used per part of DMTD. The product usually contains DMTD moieties in amounts substantially greater than the stoichiometric amount based on salt formation. If the dispersant is neutral or acidic there is, of course, no "stoichiometric amount" of DMTD and any amount thereof in the product is present in excess. If the dispersant is basic, the product usually contains at least about a five-fold excess and may contain a 500-fold or even greater excess of DMTD moieties, based on the stoichiometric amount.

The precise chemical nature of the compositions of this invention is not known. In particular, it is not certain whether a chemical reaction takes place between the DMTD and the dispersant. However, it has been shown that DMTD may be dispersed to form a homogeneous composition at lower temperatures than those prescribed for the formation of the compositions of this invention. When the former composition is heated, a solid product precipitates and upon further heating at a higher temperature, it is redispersed to form a stable, homogeneous composition. Hydrogen sulfide evolution is noted as the product precipitates when the temperature is raised. It is believed that the initial stage in this process is the homogenization of DMTD by the dispersant, and that the DMTD subsequently condenses to form dimers and other oligomers which first precipitate and are then redispersed as the temperature rises. Since the normal operating temperatures of an internal combustion engine are higher than the temperature of precipitation, the dispersions first formed are not stable enough to serve as lubricant additives, and it is necessary to go through the precipitation and redispersion steps to form an additive of this invention.

The preparation of the compositions of this invention is illustrated by the following examples. All parts and percentages are by weight. The weight ratios of dispersant to DMTD referred to are, in each instance, initial ratios. Equivalents of base in the dispersant are calculated from the base number. Equivalents of DMTD are based on an equivalent weight of 75 (one-half the molecular weight).

EXAMPLE 26

Six thousand parts of the product of Example 10 (0.64 equivalent of base) is heated to 100° C., and 484 parts of wet DMTD (420 parts on a dry basis, or 5.6 equivalents) is added over 15 minutes, with stirring. The mixture is heated at 110°–120° for 6 hours under nitrogen, during which time hydrogen sulfide evolution is noted. Mineral oil, 1200 parts, is added and the mixture is filtered while hot. The filtrate is a 53% solution of the desired product in oil and contains 1.68% nitrogen and 2.83% sulfur. The weight ratio of dispersant to DMTD is 8.6.

EXAMPLE 27

DMTD (5.6 equivalents) is prepared by adding 447 parts of carbon disulfide over 2¾ hours to a mixture of 140 parts of hydrazine hydrate, 224 parts of 50% aqueous sodium hydroxide and 1020 parts of mineral oil, with stirring under nitrogen at 25°–46° C., heating the resulting mixture at 96°–104° C. for about 3 hours, and then cooling to 78° C. and acidifying with 280 parts of 50% aqueous sulfuric acid. The resulting material is heated to 94° C. and 6000 parts of the product of Example 10 (0.64 equivalent of base) is added over about ½ hour at 90°–94° C., under nitrogen. The mixture is heated gradually to 150° C. and maintained at that temperature for about 3 hours; it is then filtered while hot to yield a 50% solution in mineral oil of the desired product. The solution contains 2.06% nitrogen and 3.26% sulfur, and the weight ratio of dispersant to DMTD therein is 8.6.

EXAMPLE 28

One thousand parts of the product of Example 1 (0.89 equivalent of base) is heated to 95° C., under nitrogen, and 288 parts of wet DMTD (250 parts on a dry basis, or 3.33 equivalents) is added over about 20 minutes. The mixture is heated to 150° C. and held at that temperature for about 5 hours, and is then filtered while hot to yield the desired product, a 59% solution in oil containing 4.61% nitrogen and 9.19% sulfur. The weight ratio of dispersant to DMTD is 2.4.

EXAMPLE 29

Following the procedure of Example 28, a product is prepared from 200 parts each of the dispersant of Example 1 (0.18 equivalent of base) and DMTD (2.67 equivalents), and 2000 parts of mineral oil is added. The product (a 20% solution in oil) contains 1.12% nitrogen and 3.48% sulfur, and the weight ratio of dispersant to DMTD is 0.6.

EXAMPLE 30

Following the procedure of Example 28, a product (50% solution in oil) is prepared from 7300 parts of the product of Example 11 (0.26 equivalent of base), 588 parts of wet DMTD (510 parts on a dry basis, or 6.8 equivalents) and 1250 parts of mineral oil. It contains 1.72% nitrogen and 3.08% sulfur, and the weight ratio of dispersant to DMTD is 7.86.

EXAMPLE 31

Following the procedure of Example 28, a product is prepared from 1000 parts of the product of Example 11 (0.036 equivalent of base), 241 parts (3.21 equivalents) of DMTD and 310 parts of mineral oil. The product is a 50% solution in mineral oil and contains 2.74% nitrogen and 6.79% sulfur. The ratio of dispersant to DMTD is 2.62.

EXAMPLE 32

Following the procedure of Example 27, DMTD (8.16 equivalents) is prepared from 204 parts of hydrazine hydrate, 324 parts of 50% aqueous sodium hydroxide, 648 parts of carbon disulfide, 1200 parts of mineral oil and 408 parts of 50% aqueous sulfuric acid. It is then reacted with 600 parts of the product of Example 11 (0.02 equivalent of base) in the presence of 600 parts of toluene, and the toluene and water are removed by azeotropic distillation to yield a product (50% solution in mineral oil) containing 1.8% nitrogen and 5.1% sulfur, and having a 5.5:1 ratio of dispersant to DMTD.

EXAMPLE 33

Following the procedure of Example 27, DMTD (5.6 equivalents) is prepared from 140 parts of hydrazine hydrate, 447 parts of carbon disulfide, 224 parts of 50% aqueous sodium hydroxide, 280 parts of 50% aqueous sulfuric acid and 1020 parts of mineral oil. It is then reacted with 6000 parts of the product of Example 11 (0.22 equivalent of base) to yield a product (50% solution in oil) containing 1.35% nitrogen and 2.64% sulfur, and having a weight ratio of dispersant to DMTD of 7.86.

EXAMPLE 34

Hydrazine hydrate, 28 parts, is mixed with 45 parts of 50% aqueous sodium hydroxide and 206 parts of mineral oil, and 102 parts of carbon disulfide is added over 2 hours. An exothermic reaction takes place which causes the temperature to rise to 38° C. The mixture is heated to 109° C. and maintained at that temperature for 1 hour, during which time hydrogen sulfide evolution is noted. It is then cooled to 88° C. and 88 parts of 33% aqueous sulfuric acid is added over ½ hour. The temperature rises to 90° C. during this addition.

The resulting slurry (1.12 equivalents of DMTD) is added to 1209 parts (0.043 equivalent of base) of the dispersant of Example 11. Volatile materials are removed by vacuum stripping at 150° C. and the remaining mixture is heated for 3 hours at that temperature. The residue is filtered while hot and the filtrate is the desired product containing 1.43% nitrogen and 2.90% sulfur, and having a weight ratio of dispersant to DMTD of 7.86.

EXAMPLE 35

A mixture of 1000 parts of the dispersant of Example 11 (0.036 equivalent of base) and 170 parts of mineral oil is heated to 70° C., and a solution of 70 parts (0.93 equivalent) of DMTD in 865 parts of isopropyl alcohol is added over about ½ hour, with stirring. Heating at 70° C. is continued as the isopropyl alcohol is stripped under vacuum, yielding a homogeneous mixture. This mixture is gradually heated to 155° C.; during the heating, a solid precipitates and a sample thereof is removed and analyzed. Elemental analysis indicates that it is an oligomer of DMTD, principally a dimer.

As heating continues above 140° C., the solid is gradually solubilized to yield a homogeneous product again. This product is the desired material (50% solution in oil) having a dispersant to DMTD ratio of 7.86:1.

As previously mentioned, the compositions of this invention are principally useful for the inhibition of copper activity and "lead paint" deposition in lubricants. They may also be used as extreme pressure agents and corrosion inhibitors for copper-lead bearings. They can be employed in a variety of lubricating compositions based on diverse oils of lubricating viscosity, including the natural and synthetic lubricating oils and mixtures thereof disclosed hereinabove as suitable oleaginous diluents. The lubricating compositions contemplated include principally crankcase lubricating oils for spark-ignited and compression-ignited internal combustion engines including automobile and truck engines, two-cycle engine lubricants, aviation piston engines, marine and railroad diesel engines, and the like. However, automatic transmission fluids, transaxle lubricants, gear lubricants, metal-working lubricants, hydraulic fluids, and other lubricating oil and grease compositions can benefit from the incorporation of the present compositions.

In general, about 0.05–20.0 parts (by weight) of the composition of this invention is dissolved in 100 parts of oil to produce a satisfactory lubricant. The invention also contemplates the use of other additives in combination with the products of this invention. Such additives include, for example, detergents and dispersants of the ash-containing or ashless type, oxidation inhibiting agents, pour point depressing agents, extreme pressure agents, color stabilizers and anti-foam agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkyl-phenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-β-naphthylamine, and dodecylamine. A particularly effective method for preparing the basic salts comprises mixing an acid with an excess of a basic alkaline earth metal neutralizing agent, a phenolic promoter compound, and a small amount of water and carbonating the mixture at an elevated temperature such as 60–200° C.

Ashless detergents and dispersants are illustrated hereinabove.

Extreme pressure agents and corrosion and oxidation inhibiting agents are exemplified by chlorinated aliphatic hydrocarbons such as chlorinated wax; organic sulfides and polysulfides such as benzyl disulfide, bis(-chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

It is possible to form the lubricants of this invention by dissolving the various additives, or oil solutions thereof, directly in a mineral oil. However, it is generally more convenient and is preferred to prepare additive concentrates comprising a diluent (typically mineral oil) and one or more of the desired additives, the latter comprising up to about 90% by weight of the concentrate, and to dissolve these concentrates in mineral oil to form the final lubricating composition.

Typical lubricating compositions according to this invention are listed in Tables II and III. All amounts listed, except those for mineral oil, are exclusive of oil present as diluent.

TABLE II

| Ingredient | Lubricant A | B | C | D |
|---|---|---|---|---|
| SAE 30 mineral oil base | 93.01 | — | 93.81 | — |
| SAE 10W-30 mineral oil base | — | 92.74 | — | — |
| SAE 10W-40 mineral oil base | — | — | — | 86.82 |
| SAE 10W-50 mineral oil base | — | — | — | — |
| Product of Example 26 | — | — | — | 10.00 |
| Product of Example 30 | — | 2.10 | — | — |
| Product of Example 33 | — | — | 2.12 | — |
| Product of Example 34 | 2.14 | — | — | — |
| Basic calcium petroleum sulfonate | — | 0.74 | 0.40 | — |
| Basic magnesium petroleum sulphonate | 0.15 | — | — | — |
| Dispersant of Example 10 | — | 0.06 | — | 0.10 |
| Dispersant of Example 11 | 1.73 | 1.16 | — | — |
| Tetrapropenyl succinic acid anhydride | 0.17 | — | 0.21 | — |
| Sulfurized reaction product of butadiene and butyl acrylate | 0.65 | 0.49 | 0.39 | — |
| Sulfurized mixture of soybean oil, tall oil acid and $C_{12-20}$ α-olefins | 1.64 | — | — | — |
| Zinc isooctylphosphorodithioate | — | — | — | — |
| Zinc salt of mixture of isobutyl- and amylphosphorodithioic acids | — | 0.83 | — | — |
| Reaction product of zinc 4-methyl-sec-amylphosphorodithioate with propylene oxide | — | — | 0.95 | — |
| Hindered phenol antioxidant | 0.33 | — | — | — |
| Polyethoxylated octylphenol | 0.18 | — | 0.23 | — |
| Poly-(isodecyl acrylate) | — | 1.88 | — | 3.08 |
| Silicone anti-foam agent | 0.006 | 0.004 | 0.006 | 0.004 |

TABLE III

| Ingredient | Lubricant E | F | G | H | J | K |
|---|---|---|---|---|---|---|
| SAE mineral oil base | — | 93.93 | 94.68 | — | — | — |
| SAE 10W-40 mineral oil base | 89.93 | — | — | 87.20 | 87.64 | 90.36 |
| Product of Example 26 | — | — | — | — | — | 1.00 |
| Product of Example 32 | — | — | — | 2.13 | — | — |
| Product of Example 33 | — | — | — | — | 2.13 | — |
| Product of Example 34 | 2.16 | 2.12 | 0.53 | — | — | — |
| Basic magnesium petroleum sulfonate | — | 0.45 | 0.14 | — | — | — |
| Dispersant of Example 10 | 0.11 | — | — | 0.11 | 0.11 | 0.11 |
| Dispersant of Example 11 | — | 1.89 | 2.52 | — | — | — |
| Dispersant of Example 18 | 1.98 | — | — | 2.39 | 2.39 | — |
| Reaction product of 1 equivalent of polyisobutenyl succinic anhydride with 2 equivalents of polyethylene polyamine mixture, further reacted with boric acid | — | — | 0.37 | — | — | — |
| Reaction product of polyisobutenyl acrylic acid with pentaethylene hexamine | — | — | — | 0.94 | 0.94 | 0.95 |
| Tetrapropenyl succinic anhydride | 0.64 | 0.21 | — | — | — | — |
| Tetrapropenyl succinic acid | — | — | 0.17 | — | 0.34 | — |
| Lithium polyisobutenyl succinate | — | — | — | 1.73 | 0.95 | 2.90 |
| Sulfurized reaction product of butadiene and butyl acrylate | — | 0.39 | 0.39 | 1.33 | 1.33 | 1.33 |
| Zinc isooctylphosphorodithioate | — | — | 1.02 | — | — | — |
| Zinc salt of mixture of isobutyl- and primary amylphosphorodithioic acids | — | 0.78 | — | — | — | — |
| Reaction product of phosphorized hydroxypropyl 4-methyl-sec-amylphosphorodithioic acid with $C_{11-14}$ tertiary alkyl primary amine mixture | — | — | — | 0.58 | 0.58 | — |
| Hindered phenol antioxidant | — | — | — | 0.49 | 0.49 | 0.25 |
| Polyethoxylated octylphenol | — | 0.23 | 0.18 | — | — | — |
| Poly-(isodecyl acrylate) | — | — | — | 3.10 | 3.10 | 3.10 |
| Silicone anti-foam agent | 0.004 | 0.006 | 0.006 | 0.004 | 0.004 | 0.004 |

What is claimed is:

1. A composition obtained by preparing a mixture comprising at least one ashless dispersant soluble in a lubricating oil and at least one dimercaptothiadiazole and heating said mixture at about 100°–250° C. until it is capable of forming a homogeneous blend with an oleaginous liquid of lubricating viscosity; about 0.1–10 parts by weight of said dispersant being present per part of said dimercaptothiadiazole.

2. A composition according to claim 1 wherein the amount of dimercaptothiadiazole is substantially greater than the stoichiometric amount based on formation of a salt thereof with said dispersant.

3. A composition according to claim 2 wherein the dimercaptothiadiazole is 2,5-dimercapto-1,3,4-thiadiazole.

4. A composition according to claim 3 wherein the mixture also contains said oleaginous liquid of lubricating viscosity.

5. A composition according to claim 4 wherein the dispersant is selected from the group consisting of carboxylic dispersants, amine dispersants, Mannich dispersants and polymeric dispersants.

6. A composition according to claim 5 wherein the dispersant is a carboxylic dispersant characterized by the presence within its molecular structure of (A) at least one acyl, acyloxy or acylimidoyl radical containing at least about 30 carbon atoms, and (B) at least one radical in which a nitrogen or oxygen atom is attached directly to said radical A, said nitrogen or oxygen atom also being attached to a hydrocarbon or substituted hydrocarbon radical.

7. A composition according to claim 6 wherein the oleaginous liquid is a mineral oil.

8. A composition according to claim 7 wherein the dispersant has a base number less than 7 or an acid number when titrated to a bromphenol blue end point, has said radicals A and B connected through linkages selected from the group consisting of amide, imide, amidine, amine salt and ester linkages, and is prepared by the reaction of a substantially saturated succinic acid, anhydride, acid halide, ester, amide, imide or amidine containing a hydrocarbon or substituted hydrocarbon radical with at least one of an alcohol and an alkylene polyamine.

9. A composition according to claim 8 wherein the dispersant is a mixed oxygen- and nitrogen-bridged dispersant prepared by sequentially reacting a succinic acid, anhydride, acid halide, ester, amide, imide or amidine having a hydrocarbon substituent which contains at least about 50 carbon atoms with at least one alcohol and at least one alkylene polyamine.

10. A composition according to claim 9 wherein the hydrocarbon substituent on the succinic acid, anhydride, acid halide, ester, amide, imide or amidine is a polyisobutenyl substituent.

11. A lubricating composition comprising a major amount of a lubricating oil and a minor amount, suitable to inhibit copper activity and "lead paint" deposition, of a composition according to claim 1.

12. A lubricating composition comprising a major amount of a lubricating oil and a minor amount, suitable to inhibit copper activity and "lead paint" deposition, of a composition according to claim 3.

13. A lubricating composition comprising a major amount of a lubricating oil and a minor amount, suitable to inhibit copper activity and "lead paint" deposition, of a composition according to claim 7.

14. A lubricating composition comprising a major amount of a lubricating oil and a minor amount, suitable to inhibit copper activity and "lead paint" deposition, of a composition according to claim 8.

15. A lubricating composition comprising a major amount of a lubricating oil and a minor amount, suitable to inhibit copper activity and "lead paint" deposition, of a composition according to claim 10.

16. A composition obtained by preparing a mixture comprising:
   2,5-dimercapto-1,3,4-thiadiazole;
   a mineral oil; and
   a dispersant which is soluble in said mineral oil and which has a base number less than 7 or an acid number when titrated to a bromphenol blue end point,
   said dispersant being prepared by sequentially reacting a polyisobutenyl-substituted succinic acid in which the polyisobutenyl substituent contains at least about 50 carbon atoms with pentaerythritol and a polyethylene polyamine containing about 3–7 amino groups per molecule;
   and heating said mixture at about 100°–250° C. until it forms a homogeneous blend;
   about 0.1°–10 parts by weight of said dispersant being present per part of 2,5-dimercapto-1,3,4-thiadiazole.

17. A lubricating composition comprising a major amount of a lubricating oil and about 0.05–20.0 parts by weight, per 100 parts of said lubricating oil, of a composition according to clam 16.

* * * * *